United States Patent [19]

Anton

[11] Patent Number: 5,176,757
[45] Date of Patent: Jan. 5, 1993

[54] 1,1,2,2,3,3-HEXAFLUOROCYCLOPENTANE AND USE THEREOF IN COMPOSITIONS AND PROCESSES FOR CLEANING

[75] Inventor: Douglas R. Anton, Claymont, Del.

[73] Assignee: E. I. Du Pont de Nemours and Company, Wilmington, Del.

[21] Appl. No.: 783,648

[22] Filed: Oct. 28, 1991

Related U.S. Application Data

[62] Division of Ser. No. 592,174, Oct. 9, 1990, Pat. No. 5,084,199, which is a division of Ser. No. 489,275, Mar. 5, 1990, abandoned.

[51] Int. Cl.$^5$ .............................................. B08B 3/04
[52] U.S. Cl. ....................................... 134/42; 134/40; 252/170; 252/DIG. 9
[58] Field of Search ................... 134/40, 42; 252/170, 252/DIG. 9

[56] References Cited

U.S. PATENT DOCUMENTS

| | | | |
|---|---|---|---|
| 2,449,233 | 9/1948 | Kischitz et al. | 260/648 |
| 2,999,815 | 9/1961 | Eiseman | 252/171 |
| 2,999,817 | 9/1961 | Bower | 252/172 |
| 3,573,213 | 3/1971 | Burt | 252/172 |
| 3,634,274 | 1/1972 | Barton et al. | |
| 3,686,130 | 8/1972 | Barton et al. | |
| 3,728,268 | 4/1973 | Burt | 252/170 |
| 3,789,006 | 1/1974 | McMillan et al. | 252/171 |
| 3,881,949 | 5/1975 | Brock | 134/31 |
| 3,903,009 | 9/1975 | Bauer et al. | 252/171 |
| 4,378,303 | 3/1983 | Hisamoto et al. | |
| 4,715,900 | 12/1987 | Connon et al. | 134/31 |
| 4,902,839 | 2/1990 | Bielefeldt et al. | 570/175 |
| 4,954,666 | 9/1990 | Bielefeldt et al. | 570/132 |
| 5,084,199 | 1/1992 | Anton | 252/170 |

FOREIGN PATENT DOCUMENTS 3735467 5/1989 Fed. Rep. of Germany.

OTHER PUBLICATIONS

Evans, et al. "Fluorocyclohexanes. Part VIII. Lithium Aluminum Hydroxide Reduction of Decafluorocyclohexene " J. Chem. Soc., 1963, pp. 4828-4834.

Burdon, et al. "Fluorocyclopentanes. Part III. The Isomeric 1H:2H:3H— and 1H:2H:4H—Heptafluorocyclopentanes and the 1H:2H:3H:4H—Hexafluorocyclopentanes " J. Chem. Soc., 1965, pp. 2382-2391.

Banks, et al., "Heterocyclic Polyfluoro-Compounds Part XIV Catalytic Hydrogenation of Perfluoro-(3-,6-dihydro-2-methyl-2H-1,2-oxazine) and of perfluorocyclopentene" J. CHem. Soc. (C), 1968, pp. 548-550.

*Primary Examiner*—Asok Pal

[57] ABSTRACT

The compound 1,1,2,2,3,3-hexafluorocyclopentane and mixtures thereof with alcohols, ethers, esters, ketones, nitromethane, and halogenated hydrocarbons are disclosed; as is a process for cleaning a solid surface which comprises treating the surface with said compound or said mixtures. Binary mixtures of 1,1,2,2,3,3-hexafluorocyclopentane either with about 27 to 35 weight percent methanol, or with about 21 to 29 weight percent ethanol are disclosed as azeotrope or azeotrope-like compositions and are particularly suited for use where solvent recovery and reuse is practiced.

20 Claims, No Drawings

1,1,2,2,3,3-HEXAFLUOROCYCLOPENTANE AND USE THEREOF IN COMPOSITIONS AND PROCESSES FOR CLEANING

This is a division of application Ser. No. 07/592,174, filed Oct. 9,1990 and issued on Jan. 28, 1992 as U.S. Pat. No. 5,084,199, which is a division of application Ser. No. 07/489,275, filed Mar. 5, 1990, now abandoned.

FIELD OF THE INVENTION

This invention relates to halogen substituted hydrocarbon compounds, their compositions and uses, and more particularly to fluorine-substituted hydrocarbons, their mixtures with solvents such as ethanol or methanol, and the use thereof for cleaning solid surfaces.

BACKGROUND OF THE INVENTION

Various organic solvents have been used as cleaning liquids for the removal of contaminants from contaminated articles and materials. Certain fluorinecontaining organic compounds such as 1,1,2-trichloro-1,2,2-trifluoroethane have been reported as useful for this purpose, particularly with regard to cleaning organic polymers and plastics which may be sensitive to other more common and more powerful solvents such as trichloroethylene or perchloroethylene. Recently, however, there have been efforts to reduce the use of certain compounds such as trichlorotrifluoroethane which also contain chlorine because of a concern over their potential to deplete ozone, and to thereby affect the layer of ozone that is considered important in protecting the Earth's surface from ultraviolet radiation.

Boiling point, flammability and solvent power can often be adjusted by preparing mixtures of solvents. For example, certain mixtures of 1,1,2-trichloro-1,2,2-trifluoroethane with other solvents (e.g. isopropanol and nitromethane) have been reported as useful in removing contaminants which are not removed by 1,1,2-trichloro-1,2,2-trifluoroethane alone, and in cleaning articles such as electronic circuit boards where the requirements for a cleaning solvent are relatively stringent, (i.e. it is generally desirable in circuit board cleaning to use solvents which have low boiling points, are non-flammable, have low toxicity, and have high solvent power so that flux such as rosin and flux residues which result from soldering electronic components to the circuit board can be removed without damage to the circuit board substrate).

While boiling, flammability, and solvent power can often be adjusted by preparing mixtures of solvents, the utility of the resulting mixtures can be limited for certain applications because the mixtures fractionate to an undesirable degree during use. Mixtures can also fractionate during recovery, making it more difficult to reuse a solvent mixture with the original composition. Azeotropic compositions, with their constant boiling and constant composition characteristics, are thus considered particularly useful.

Azeotropic compositions exhibit either a maximum or minimum boiling point and do not fractionate upon boiling. These characteristics are also important in the use of the solvent compositions in certain cleaning operations, such as removing solder fluxes and flux residues from printed circuit boards. Preferential evaporation of the more volatile components of the solvent mixtures, which would be the case if the mixtures were not azeotropes, or azeotrope-like, would result in mixtures with changed compositions which may have less desirable properties (e.g. lower solvency for contaminants such as rosin fluxes and/or less inertness toward the substrates such as electrical components).

Azeotropic characteristics are also desirable in vapor degreasing operations where redistilled material is usually used for final rinse-cleaning. Thus, the vapor defluxing or degreasing system acts as a still. Unless the solvent composition exhibits a constant boiling point (i.e. is an azeotrope or is azeotrope-like) fractionation will occur and undesirable solvent distribution may act to upset the safety and effectiveness of the cleaning operation.

A number of azeotropic compositions based upon halohydrocarbons containing fluorine have been discovered and in some cases used as solvents for the removal of solder fluxes and flux residues from printed circuit boards and for miscellaneous vapor degreasing applications. For example, U.S. Pat. No. 2,999,815 discloses the azeotrope of 1,1,2-trichloro-1,2,2-trifluoroethane with acetone; U.S. Pat. No. 3,903,009 discloses a ternary azeotrope of 1,1,2-trichloro-1,2,2-trifluoroethane with nitromethane and ethanol; U.S. Pat. No. 3,573,213 discloses an azeotrope of 1,1,2-trichloro-1,2,2-trifluoroethane with nitromethane; U.S. Pat. No. 3,789,006 discloses the ternary azeotrope of 1,1,2-trichloro-1,2,2-trifluoroethane with nitromethane and isopropanol; U.S. Pat. No. 3,728,268 discloses the ternary azeotrope of 1,1,2-trichloro-1,2,2-trifluoroethane with acetone and ethanol; U.S. Pat. No. 2,999,817 discloses the binary azeotrope of 1,1,2-trichloro-1,2,2-trifluoroethane and methylene chloride; and U.S. Pat. No. 4,715,900 discloses ternary compositions of trichlorotrifluoroethane, dichlorodifluoroethane, and ethanol or methanol.

As noted above, many solvent compositions which have proven useful for cleaning contain at least one component which is a halogen-substituted hydrocarbon containing chlorine, and there have been concerns raised over the ozone depletion potential of halogen-substituted hydrocarbons which contain chlorine. Efforts are being made to develop compositions which may at least partially replace the chlorine containing components with other components having lower potential for ozone depletion. Azeotropic compositions of this type are of particular interest.

Unfortunately, as recognized in the art, it is not possible to predict the formation of azeotropes and this obviously complicates the search for new azeotropic systems which have application in this field. Nevertheless, there is a constant effort in the art to discover new azeotropes or azeotrope-like systems which have desirable solvency characteristics and particularly a greater versatility of solvency power.

SUMMARY OF THE INVENTION

This invention provides a novel fluorohydrocarbon compound, 1,1,2,2,3,3-hexafluoro-cyclopentane, and mixtures thereof with miscible solvents such as alcohols (e.g. methanol, ethanol, isopropanol, etc.), ethers (e.g. tetrahydrofuran, etc.), esters, ketones (e.g. acetone), nitromethane, and halogenated hydrocarbons (e.g. methylene chloride, 1,1,2-trichloro-1,2,2-trifluoroethane, dichlorodifluoroethane, trans-1,2-dichloroethylene, etc.). Mixtures with miscible solvents which form an azeotrope or azeotrope-like composition are preferred; and most preferred are mixtures of compounds which contain no chlorine. There is provided in accordance with this invention an azeotrope or azeotrope-like composition comprising an admixture of effective amounts of 1,1,2,2,3,3-hexafluorocyclopentane and an alcohol selected from a group consisting of methanol and ethanol and, more specifically, an admixture of either about 69 weight percent 1,1,2,2,3,3-hexafluorocyclopentane and about 31 weight percent methanol, or about 75 weight percent 1,1,2,2,3,3-hexafluorocyclopentane and about 25 weight percent ethanol.

The compound, 1,1,2,2,3,3-hexafluorocyclopentane, and its azeotropic compositions with solvents such as methanol and ethanol are well suited for solvent cleaning applications.

DETAILED DESCRIPTION OF THE INVENTION

A novel fluorohydrocarbon compound, 1,1,2,2,3,3-hexafluorocyclopentane is provided in accordance with this invention. The designation of this compound in conventional nomenclature for halogen-substituted hydrocarbons containing fluorine is C456ff. C456ff may be prepared by mixing together 1,2-dichloro-hexafluorocyclopent-1-ene (available commercially), an alkali metal acetate, Pd on carbon (a commercially available catalyst), and excess hydrogen gas and reacting the mixture at a temperature in the range of about 0° C. to 200° C. and a pressure within the range of about 15 psig to 2000 psig for from about 5 to 30 hours. The reaction can be carried out in a pressure vessel such as a Parr shaker or an autoclave. Generally, after completion of the reaction, the crude product is filtered to remove catalyst, washed with water to remove acetic acid, treated with magnesium sulfate to remove excess water, then distilled to give pure C4356ff with a one degree boiling point range. C456ff is a liquid under ambient conditions and is considered useful as a solvent which can be employed for cleaning contaminants from solid substrates.

C456ff is miscible with various solvents conventionally used in cleaning operations. Compositions suitable for use in cleaning operations can be prepared which comprise a mixture of C456ff with one or more compounds selected from the group consisting of alcohols, ethers, esters, ketones, nitromethane, and halogenated hydrocarbons. The preferred alcohols and halogenated hydrocarbons contain from 1 to 4 carbon atoms; the preferred ethers contain from 2 to 4 carbon atoms; and the preferred esters and ketones contain from 3 to 4 carbon atoms. Examples of suitable alcohols include methanol, ethanol and isopropanol. Examples of suitable ethers include tetrahydrofuran. Examples of suitable ketones include acetone. Examples of suitable halogenated hydrocarbons include methylene chloride, 1,1,2-trichloro-1,2,2-trifluoroethane, dichlorodifluoroethane and trans-1,2-dichloroethylene. Preferably, such compositions contain at least about 5 percent by weight of C456ff; and can contain up to 95 percent by weight, or even more of C456ff. Most preferred with respect to ozone depletion potential are compositions in which all components contain no chlorine.

A composition which comprises an admixture of effective amounts of C456ff and one or more solvents selected from the group consisting of alcohols, ethers, esters, ketones, nitromethane and halogenated hydrocarbons to form an azeotrope or azeotrope-like mixture, are considered especially useful. Compositions which are mixtures of C456ff with alcohol selected from the group consisting of methanol and ethanol are preferred.

By azeotrope or azeotrope-like is meant constant boiling liquid admixtures of two or more substances which admixtures behave like a single substance in that the vapor produced by partial evaporation or distillation has the same composition as the liquid, i.e., the admixtures distill without a substantial change in composition. Constant boiling compositions characterized as azeotropes or azeotrope-like exhibit either a maximum or minimum boiling point as compared with that of nonazeotropic mixtures of the same substances.

By effective amounts is meant the amounts of each component of the admixture of the instant invention, which, when combined, results in the formation of the azeotrope or azeotrope-like admixture of the instant invention.

It is possible to fingerprint, in effect, a constant boiling admixture, which may appear under varying guises depending on the conditions chosen, by any of several criteria.

The composition may be defined as an azeotrope of its components, say component A and component B, since the very term "azeotrope" is at once both definitive and limitive, requiring that effective amounts of A and B form this unique composition of matter which is a constant boiling admixture. It is well known by those who are skilled in the art that at differing pressures, the composition of a given azeotrope will vary, at least to some degree, and changes in distillation pressures also change, at least to some degree, the distillation temperatures. Thus, an azeotrope of A and B represents a unique type of relationship but with a variable composition depending on temperature and/or pressure. Therefore, compositional ranges, rather than fixed compositions, are often used to define azeotropes.

Or, the composition can be defined as a particular weight relationship or mole percent relationship of A and B, while recognizing that such specific values point out only one particular such relationship and that in actuality a series of such relationships represented by A and B actually exist for a given azeotrope, varied by influence of distillative conditions of temperature and pressure.

Or, recognizing that the azeotrope A and B does represent just such a series of relationships, the azeotropic series represented by A and B can be characterized by defining the composition as an azeotrope characterized by a boiling point at a given pressure, thus giving identifying characteristics without unduly limiting the scope of the invention by a specific numerical composition, which is limited by and is only as accurate as the analytical equipment available.

Azeotrope or azeotrope-like compositions are provided in accordance with this invention which comprise admixtures of effective amounts of C456ff with an alcohol selected from the group consisting of methanol and ethanol to form an azeotrope or azeotrope-like mixture.

In accordance with this invention, compositions which are binary mixtures of from about 65 to 73 weight percent C456ff and from about 27 to 35 weight percent methanol are characterized as azeotropes or azeotrope-like in that mixtures within this range exhibit a substantially constant boiling point. Being substantially constant boiling, the mixtures do not tend to fractionate to any great extent upon evaporation. After evaporation, only a small difference exists between the composition of the vapor and the composition of the initial liquid phase. This difference is so small that the compositions of the vapor and liquid phases are considered substantially identical. Accordingly, any mixture within this range exhibits properties which are characteristic of a true binary azeotrope. The binary composition consisting essentially of about 69 weight percent C456ff and about 31 weight percent methanol has been established, within the accuracy of the fractional distillation method, as a true binary azeotrope, boiling at about 61° C. at substantially atmospheric pressure and is the preferred azeotrope of this invention.

Also, in accordance with this invention, compositions which are binary mixtures of from about 71 to 79 weight percent C456ff and from about 21 to 29 weight percent ethanol are characterized as an azeotrope or azeotrope-like in that mixtures within this range exhibit a substantially constant boiling point. Being substantially constant boiling, the mixtures do not tend to fractionate to any great extent upon evaporation. After evaporation, only a small difference exists between the composition of the vapor and the composition of the initial liquid phase. This difference is so small that the compositions of the vapor and liquid phases are considered substantially identical. Accordingly, any mixture within this range exhibits properties which are characteristic of a true binary azeotrope. The binary composition consisting essentially of about 75 weight percent C456ff and about 25 weight percent ethanol has been established, within the accuracy of the fractional distillation method, as a true binary azeotrope, boiling at about 71° C. at substantially atmospheric pressure and is the preferred azeotrope of this invention.

C456ff, its azeotropes with methanol and ethanol, and other mixtures of this invention are useful in a wide variety of processes for cleaning solid surfaces which comprise treating said surface therewith. Applications include removal of flux and flux residues from printed circuit boards contaminated therewith.

The compositions of the invention may be used in conventional apparatus, employing conventional operating techniques. The solvent(s) may be used without heat if desired, but the cleaning action of the solvent may be applied by conventional means (e.g. heating, agitation, etc.). In some applications (e.g. removing certain tenacious fluxes from soldered components) it may be advantageous to use ultrasonic irradiation in combination with the solvent(s).

The azeotropes of the present invention permit easy recovery and reuse of the solvent from vapor defluxing and degreasing operations because of their azeotropic nature. As an example, compositions provided in accordance with this invention can be used in cleaning processes such as is described in U.S. Pat. No. 3,881,949 and U.S. Pat. No. 4,715,900, both of which are incorporated herein by reference.

The azeotropes and other mixtures of the instant invention can be prepared by any convenient method including mixing or combining the desired amounts of the components. A preferred method is to weigh the desired amounts of each component and thereafter combine them in an appropriate container.

Practice of the invention will become further apparent from the following non-limiting examples.

EXAMPLE 1

1,2-dichlorohexafluorocyclopent-1-ene (215 g) was added to a 400 ml shaker tube along with sodium acetate (20 g) and 5% palladium on carbon (1 g). The shaker tube was cooled, evacuated, and pressurized with hydrogen to 50 psig at room temperature. It was then heated to 100° C., and the hydrogen pressure was adjusted to 500 psig. It was held at 100° C. for 12 hours with periodic additions of hydrogen to maintain a pressure of 500 psig. The shaker tube was then cooled and bled of excess hydrogen. The product was filtered to remove catalyst, washed with 20 ml of water, and dried over $MgSO_4$. This reaction gave approximately 10 ml of clear liquid. $^1H$ NMR ($HCCl_3$ as internal standard): 2.4 ppm (complex). $^{19}F$ NMR ($FCCl_3$ as internal standard): $-115.1$ (2 F), $-136.4$ (4 F). GC/IR: 2900 m, 1190 vs. Mass Spect: 178 (parent), 95 and 64 (major peaks).

EXAMPLE 2

1,2-dichlorohexafluorocyclopent-1-ene (100 g) was added to a Parr bottle along with 5% palladium on carbon (2 g), sodium acetate trihydrate (120 g), and water (100 mL). The bottle was placed in a Parr shaker, purged several times with nitrogen, purged several times with hydrogen, and held under a hydrogen pressure of 60 psig for 24 hours with shaking. The reaction mixture was then filtered to remove the catalyst and the organic layer was separated from the aqueous layer. The yield of crude C456ff was 66 g, 96% of theory. The crude product from several runs was combined, washed with water to remove acetic acid, and distilled. The pure product boiled at about 87° to 88° C.

EXAMPLE 3

25 grams of C456ff and 10 grams of methanol were combined and the mixture was distilled using a concentric tube column of the type commercially available from Ace Glass of Vineland, N.J. A constant boiling azeotrope was formed which had a boiling point of about 61.1° C. Gas chromatographic analysis showed the azeotrope consisted of 69.4% C456ff and 30.6% of methanol.

EXAMPLE 4

10 grams of C456ff and 2 grams of ethanol were combined in a flask and distilled using a concentric tube column of the type commercially available from Ace Glass of Vineland, N.J. A constant boiling azeotrope was formed which had a boiling point of about 71° C. Gas chromatographic analysis showed the azeotrope consisted of 75.4% C456ff and 24.6% ethanol.

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for cleaning a solid surface which comprises treating said surface with a composition comprising an admixture of effective amounts of 1,1,2,2,3,3-hexafluorocyclopentane and one or more solvents selected from the group consisting of alcohols containing from 1 to 4 carbon atoms to form an azeotrope or azeotrope-like mixture.

2. The process of claim 1 wherein said surface is treated with a mixture in which all components contain no chlorine.

3. The process of claim 1 wherein the solid surface is a printed circuit board contaminated with flux and flux residues.

4. The process of claim 1 which comprises treating said surface either with an azeotrope or azeotrope-like composition comprising from about 65 to 73 weight percent 1,1,2,2,3,3-hexafluorocyclopentane and from about 27 to 35 weight percent methanol, or with an azeotrope or azeotrope-like composition comprising from about 71 to 79 weight percent 1,1,2,2,3,3-hexafluorocyclopentane and from about 21 to 29 weight percent ethanol.

5. The process of claim 1 wherein the solid surface is treated with 1,1,2,2,3,3-hexafluorocyclopentane and alcohol selected from the group consisting of ethanol and methanol.

6. The process of claim 1 which comprises treating said surface with a cleaning composition consisting essentially of effective amounts of (i) 1,1,2,2,3,3-hexafluorocyclopentane and (ii) one or more solvents selected from the group consisting of alcohols containing from 1 to 4 carbon atoms, to form an azeotrope or azeotrope-like mixture which contains between about 5 and 95 percent by weight 1,1,2,2,3,3-hexafluorocyclopentane.

7. The process of claim 6 wherein said cleaning composition is a mixture of 1,1,2,2,3,3-hexafluorocyclopentane with one or more compounds selected from the group consisting of methanol, ethanol, and isopropanol.

8. The process of claim 7 in which all the components of said cleaning composition contain no chlorine.

9. The process of claim 6 in which all components of said cleaning composition contain no chlorine.

10. The process of claim 9 wherein said cleaning composition is a mixture of 1,1,2,2,3,3-hexafluorocyclopentane and alcohol selected from the group consisting of methanol and ethanol.

11. The process of claim 6 which further comprises recovering 1,1,2,2,3,3-hexafluorocyclopentane and one or more of said solvents as an azeotrope.

12. The process of claim 1 which comprises treating said surface with an azeotrope or azeotrope-like composition comprising from about 65 to 73 weight percent 1,1,2,2,3,3-hexafluorocyclopentane and from about 27 to 35 weight percent methanol.

13. The process of claim 12 which further comprises recovering 1,1,2,2,3,3-hexafluorocyclopentane and methanol as an azeotrope.

14. The process of claim 12 wherein the azeotrope or azeotrope-like composition consists essentially of about 69 weight percent 1,1,2,2,3,3-hexafluorocyclopentane and about 31 weight percent methanol.

15. The process of claim 12 wherein the azeotrope or azeotrope-like composition has a boiling point at about 61° C. at substantially atmospheric pressure.

16. The process of claim 1 which comprises treating said surface with an azeotrope or azeotrope-like composition comprising from about 71 to 79 weight percent 1,1,2,2,3,3-hexafluorocyclopentane and from about 21 to 29 weight percent ethanol.

17. The process of claim 16 which further comprises recovering 1,1,2,2,3,3-hexafluorocyclopentane and ethanol as an azeotrope.

18. The process of claim 16 wherein the azeotrope or azeotrope-like composition consists essentially of about 75 weight. percent 1,1,2,2,3,3-hexafluorocyclopentane and about 25 weight percent ethanol.

19. The process of claim 16 wherein the azeotrope or azeotrope-like composition has a boiling point of about 71° C. at substantially atmospheric pressure.

20. The process of claim 1 which further comprises recovering 1,1,2,2,3,3-hexafluorocyclopentane and one or more of said solvents as an azeotrope.

* * * * *